United States Patent [19]
Kristiansen

[11] 3,988,445
[45] Oct. 26, 1976

[54] CONTROL OF INSECTS WITH O-(METHYL OR ETHYL)-O(S)-LOWER ALKOXYL-O-(4-PHENOXYPHENYL)-PHOSPHATES

[75] Inventor: Odd Kristiansen, Mohlin, Switzerland

[73] Assignee: Ciba-Geigy Corporation, Ardsley, N.Y.

[22] Filed: Sept. 15, 1975

[21] Appl. No.: 613,138

Related U.S. Application Data
[62] Division of Ser. No. 466,923, May 6, 1974, Pat. No. 3,927,149.

[30] Foreign Application Priority Data
May 11, 1973 Switzerland.......................... 6721/73
Mar. 20, 1974 Switzerland.......................... 3884/74

[52] U.S. Cl............................. 424/217; 424/DIG. 8
[51] Int. Cl.$^2$............................................. A01N 9/36
[58] Field of Search..................... 424/217; 260/951

[56] References Cited
UNITED STATES PATENTS
3,280,227  10/1966  Mitchell et al..................... 260/951
3,833,691  9/1974  Rathgeb............................. 260/951

*Primary Examiner*—V. D. Turner
*Attorney, Agent, or Firm*—Frederick H. Rabin

[57] ABSTRACT

Phosphorus compounds of the formula

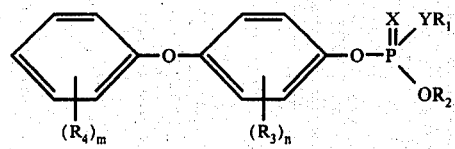

wherein $R_1$ represents alkyl with 1 to 7 carbon atoms, $R_2$ represents methyl or ethyl, $R_3$ and $R_4$ each represents hydrogen, nitro or halogen, $m = 1$ to 5 $n = 1$ to 4, and X and Y each represents oxygen or sulphur, processes for their manufacture, and a method of using them in pest control.

15 Claims, No Drawings

CONTROL OF INSECTS WITH O-(METHYL OR ETHYL)-O(S)-LOWER ALKOXYL-O-(4-PHENOXYPHENYL)-PHOSPHATES

This is a division of application Ser. No. 446,923 filed on May 6, 1974 now U.S. Pat. No. 3,927,149.

The present invention provides organic phosphorus compounds, processes for their manufacture, and a method of using them in pest control.

The phosphorus compounds have the formula

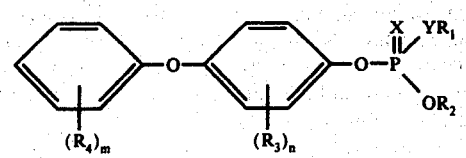

wherein $R_1$ represents alkyl with 1 to 7 carbon atoms, $R_2$ represents methyl or ethyl, $R_3$ and $R_4$ each represents hydrogen, nitro or halogen, $m = 1$ to 5 and $n = 1$ to 4, and X and Y each represents oxygen or sulphur.

Halogen is to be understood as meaning fluorine, chlorine, bromine and/or iodine, preferably chlorine and/or bromine.

The alkyl groups represented by $R_1$ can be straight-chain or branched. Examples of such groups include: methyl, ethyl, n-butyl, iso-butyl, sec. butyl and tert. butyl, n-pentyl, n-hexyl, n-heptyl and isomers thereof.

Preferred compounds on account of their action are those of the formula I wherein $R_1$ represents methyl, ethyl, n-propyl, isopropyl, n-butyl, sec. butyl, n-pentyl or n-heptyl, $R_2$ represents ethyl, $R_3$ and $R_4$ each represents hydrogen, chlorine, bromine and/or nitro, m and n are each 1 or 2, X represents oxygen or sulphur and Y represents sulphur.

The compounds of the formula I can be manufactured by the following methods which are known per se:

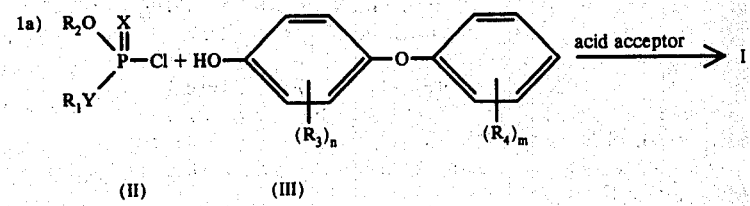

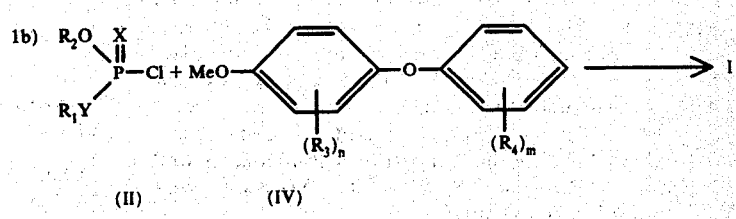

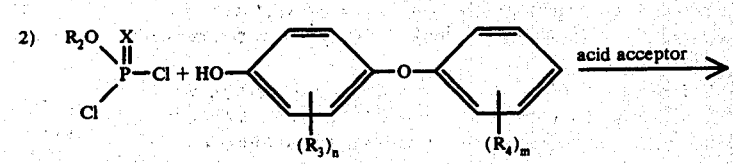

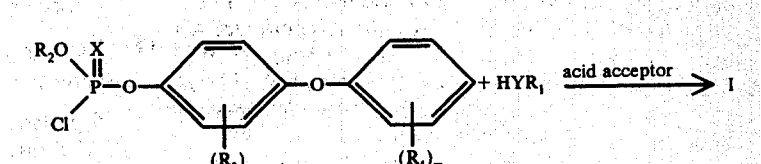

In the formulae II to IV, the symbols $R_1$ to $R_4$, m and n and X and Y have the same meanings as for the formula I and Me represents an alkali metal, in particular sodium or potassium, or represents the group $(R)_3{}^+NH$, wherein R represents hydrogen or alkyl with 1 to 4 carbon atoms.

Suitable acid acceptors are: tertiary amines, e.g. trialkylamines, pyridine, dialkyl anilines; inorganic bases, e.g. hydrides, hydroxides, carbonates and bicarbonates of alkali metals and alkaline earth metals. It is sometimes necessary to use catalysts in the reactions, e.g. copper or copper chloride. Processes 1a, 1b and 2 are carried out at a reaction temperature between −2° C and +130° C, at normal pressure, and in solvents or diluents.

Examples suitable solvents or diluents are: ethers and ethereal compounds, e.g. diethyl ether, dipropyl ether, dioxan, tetrahydrofuran; amides, e.g. N,N-dialkylated carboxy amides; aliphatic, aromatic and halogenated hydrocarbons, in particular benzene, toluene, xylene, chloroform, chlorobenzene; nitriles, e.g. acetonitrile; dimethyl sulphoxide, ketones, e.g. acetone, methyl ethyl ketone; water.

The starting materials of the formulae II, III, IV and V are known and can be manufactured in analogous manner to known methods.

The compounds of the formula I exhibit a broad biocidal activity and can be used for the control of a variety of plant and animal pests.

In particular they are suitable for combating insects of the families:

Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelisae, Coccinellidae, Bruchidae, Scarabacidae, Dermestidae, Tenebrionidae, Curulionidae, Tineidae, Noctuidae, Lymantriidae, Pyralidae, Galleridae, Culicidae, Tipulidae, Stomoxydae, Muscidae, Calliphoridae, Trypetidae, Pulicidae as well as Acaridae of the families: Ixodidae, Argasidae, Tetranchidae, Dermanyssidae.

By addition of other insecticides and/or acaricides it is possible to improve substantially the insecticidal or acaricidal action and to adapt it to given circumstances.

Examples of suitable additives are: organic phosphorus compounds, nitrophenols and derivatives thereof; formamidines; ureas; carbamates and chlorinated hydrocarbons.

In addition to the above mentioned properties, the compounds of the formula I are also active against representatives of the division Thallophyta. Thus a number of these compounds exhibit bactericidal action. But they are active chiefly against fungi, especially against phytopathogenic fungi belonging to the following classes: Oomycetes, Zygomycetes, Ascomycetes, Basidiomycetes, Denteromycetes.

The compounds of the formula I also exhibit a fungitoxic action against fungi which attack the plants from the soil. The new active substances are also suitable for treating seeds, fruit, tubers etc. from attack by fungus infections. The compounds of the formula I are also suitable for combating phytopathogenic nematodes.

The compounds of the formula I may be used as pure active substance or together with suitable carriers and/or additives. Suitable carriers and additives can be solid or liquid and correspond to the substances conventionally used in formulation technology, for example natural or regenerated substances, solvents, dispersants, wetting agents, adhesives, thickeners, binders and/or fertilizers.

For application, the compounds of the formula I may be processed to dusts, emulsion concentrates, granules, dispersions, sprays, to solutions or suspensions, in the conventional formulation which is commonly employed in application technology. Mention is also to be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances can take, and be used in, the following forms:

Solid forms:
dusts, tracking agents, granules, coated granules, impregnated granules and homogeneous granules.

Liquid forms:
a. active substances which are dispersible in water: wettable powders, pastes, emulsions:
b. solutions.

The content of active substance in the above described agents is between 0.1 to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:

a.
5 parts of active substance
95 parts of talcum b.
2 parts of active substance
1 part of highly disperse silicic acid
97 parts of talcum.

The active substances are mixed with the carriers and ground.

Granules

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3-0.8 mm).

The active substance is mixed with epichlorohydrin and dissolved with 6 parts of acetone; the polyethylene glycol and cetyl polyglycol ether are then added. The resulting solution is sprayed on kaolin, and the acetone is subsequently evaporated in vacuo.

Wettable powder:

The following constituents are used for the preparation of (a) a 40%, (b) and (c) a 25%, and (d) a 10% wettable powder:

a.
- 40 parts of active substance,
- 5 parts of sodium lignin sulphonate,
- 1 part of sodium dibutyl-naphthalene sulphonate,
- 54 parts of silicic acid.

b.
- 25 parts of active substance,
- 4.5 parts of calcium lignin sulphonate,
- 1.9 parts of Champagne chalk/hydroxyethyl cellulose mixture (1:1),
- 1.5 parts of sodium dibutyl naphthalene sulphonate,
- 19.5 parts of silicic acid,
- 19.5 parts of Champagne chalk,
- 28.1 parts of kaolin.

c
- 25 parts of active substance,
- 2.5 parts of isooctylphenoxy-polyoxyethylene-ethanol,
- 1.7 parts of Champagne chalk/hydroxyethyl cellulose mixture (1:1),
- 8.3 parts of sodium aluminium silicate,
- 16.6 parts of kieselguhr,
- 46 parts of kaolin.

d.
- 10 parts of active substance,
- 3 parts of a mixture of the sodium salts of saturated fatty alcohol sulphates,
- 5 parts of naphthalenesulphonic acid/formaldehyde condensate,
- 82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to produce (a) a 10% and (b) a 25% emulsifiable concentrate:

a.
- 10 parts of active substance,
- 3.4 parts of epoxidised vegetable oil,
- 13.4 parts of a combination emulsifier consisting of fatty alcohol polyglycol ether and alkylaryl sulphonate calcium salt,
- 40 parts of dimethylformamide,
- 43.2 parts of xylene,
- 25 parts of active substance,
- 2.5 parts of epoxidised vegetable oil,
- 10 parts of an alkylarylsulphonate/fatty alcohol-glycol ether mixture,
- 5 parts of dimethylformamide,
- 57.5 parts of xylene.

From these concentrates it is possible to produce, by dilution with water, emulsions of any desired concentration.

Spray:

The following constituents are used to prepare a 5% spray:
- 5 parts of active substance,
- 1 part of epichlorohydrin,
- 94 parts of benzene (boiling limits 160°–190° C).

EXAMPLE 1

With stirring, 41 g of O-ethyl-S-n-propylthiolphosphoric chloride in 60 ml of diethyl ether is added dropwise so rapidly to a solution, cooled to 10° C, of 37 g of 4-hydroxydiphenyl ether and 22 g of triethylamine in 500 ml of absolute diethyl ether that the temperature does not rise above 30° C. The reaction mixture is stirred for a further 2 hours at 20°–30° C and treated, with continued stirring, with 300 ml of ice water. The organic phase is isolated, shaken once with water and twice with ice cold 5% sodium hydroxide solution and then washed neutral with water.

The ethereal phase is treated with activated charcoal, filtered, dried, and the solvent is evaporated off. The oily residue is dried for 3 hours at 70° C and 0.1 Torr to yield the compound of the formula

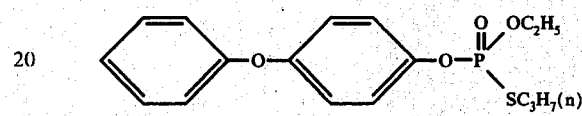

as a yellowish, non-distillable, viscous oil with a refraction of $n_D^{20°} = 1.5524$.

The following compounds are also manufactured in analogous manner:

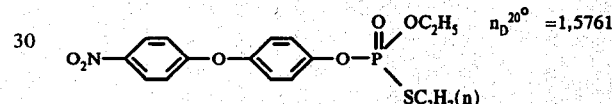

$n_D^{20°} = 1,5761$

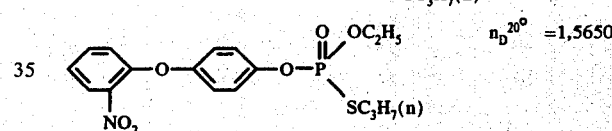

$n_D^{20°} = 1,5650$

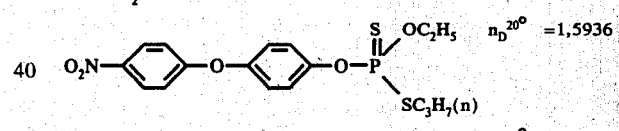

$n_D^{20°} = 1,5936$

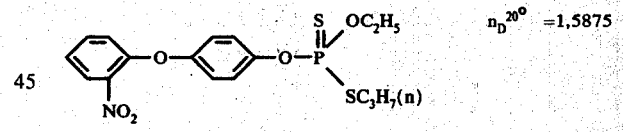

$n_D^{20°} = 1,5875$

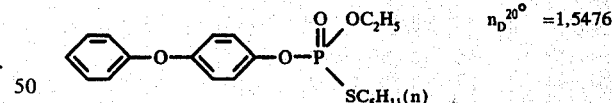

$n_D^{20°} = 1,5476$

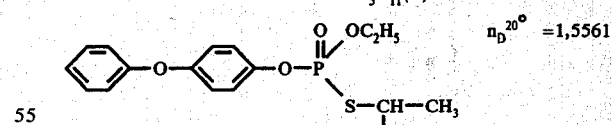

$n_D^{20°} = 1,5561$

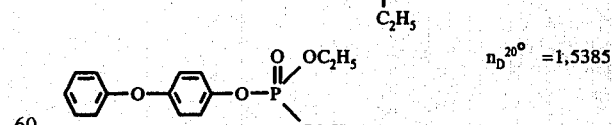

$n_D^{20°} = 1,5385$

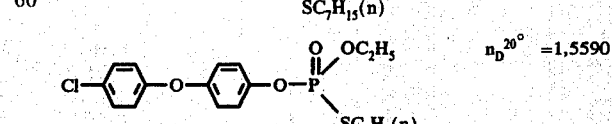

$n_D^{20°} = 1,5590$

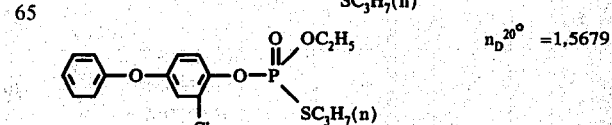

$n_D^{20°} = 1,5679$

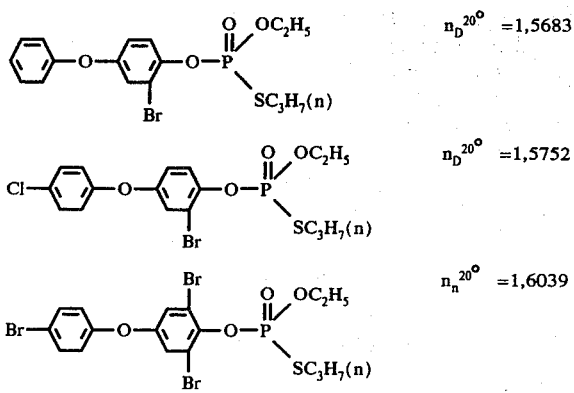

EXAMPLE 2

A. Insecticidal ingest poison action

Cotton and potato plants were sprayed with a 0.05% aqueous emulsion (obtained from a 10% emulsifiable concentrate). After the coating had dried, the cotton plants were populated with Spodoptera littoralis or Heliothis virescens larvae $L_3$ and the potato plants with Colorado potato beetle larvae (Leptinotarsa decemlineata). The test was carried out at 24° C and 60% relative humidity. In the above test, the compounds according to Example 1 displayed good ingest poison action against Spodoptera littoralis. Heliothis and Leptinotarsa decemlineata larvae.

B. System insecticidal action

To determine the systemic action, rooted bean plants (Vicia fabae) were put into a 0.01% aqueous active substance solution (obtained from a 10% emulsifiable concentrate). After 24 hours, aphide (Aphis fabae) were placed on the parts of the plant above the soil. The aphids were protected from contact and gas action by means of a special device. The test was carried out at 24° C and 70° C relative humidity. In the above test, the compounds according to Example 1 have systemic action against Aphis fabae.

EXAMPLE 3

Action against Chilo suppressalis

Six rice plants at a time of the variety Caloro were transplanted into plastic pots (diameter at the top = 17 cm) and reared to a height of about 60 cm. Infestation with Chilo suppressalis larvae ($L_1$ : 3–4 mm long) took place 2 days after the active substance had been applied in granule form to the paddy water (rate of application: 8 kg of active substance per hectare). Evaluation of the insecticidal action took place 10 days after application of the granules. The compounds according to Example 1 were active in the above test against Chilo suppressalis.

EXAMPLE 4

Sterilised compost earth was homogeneously mixed with a wettable powder containing 25% of active substance so that there resulted a rate of application of 8 kg of active substance per hectare.

Young zucchetti plants (Cucumis pepo) were put into plastic pots with the treated soil (3 plants per pot; diameter of pot = 7 cm). Each pot was infected immediately afterwards with 5 Aulacophora femoralis and Pachmoda or Chortophila larvae. The control was carried out 4, 8, 16 and 32 days after depositing the larvae.

At 80–100% kill after the first control, a fresh infestation with 5 larvae each was carried out in the same soil sample with 3 new zucchetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

In the above test, the compounds according to Example I displayed action against Aulacophora femoralis, Pachmoda and Chortophila larvae.

EXAMPLE 5

Action against ticks

A. Rhipicephalus bursa

Five adult ticks and 50 tick larvae were counted into a glass tube and immersed for 1 to 2 minutes in 2 ml of an aqueous emulsion from an emulsion series each containing 100, 10, 1 or 0.1 ppm of test substance. The tube was then sealed with a standardised cotton wool plug and placed on its head, so that the active substance emulsion could be absorbed by the cotton wool.

In the case of the adults evaluation took place after 2 weeks, and in that of the larvae after 2 days. Each test was repeated twice.

B. Boophilus microplus (larvae)

Tests were carried out in each case with 20 OP-sensitive larvae using a dilution series analogous to that of test A. (The resistance refers to the tolerability of Diazinon). The compounds according to Example 1 acted in these tests against adults and larvae of Rhipicephalus bursa and sensitive and OP-resistant larvae of Boophilus microplus.

EXAMPLE 6

Acaricidal action

Phaseolus vulgaris (dwarf beans) have an infested piece of leaf from a mass culture of Tetranychus urticae placed on them 12 hours before the test for the acaricidal action. The mobile stages which have migrated are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "interim", the treated plates are kept in greenhouse compartments at 25° C. The compounds according to Example 1 were active in the above test against eggs, larvae and adults of Tetranychus urticae.

EXAMPLE 7

Action against soil nematodes

To the test action against soil nematodes, the active substance in the concentration indicated in each case is applied to an intimately mixed with soil infected with root gall nematodes (Meloidgyne Arenaria). Immediately afterwards, tomato cuttings are planted in the thus prepared soil in a series of tests and after a waiting time of 8 days tomato seeds are sown in another test series.

In order to assess the nematocidal action the galls present on the roots are counted 28 days after planting and sowing respectively. In this test the compounds according to Example 1 display good action against *Meloidgyne arenaria*.

I claim:

1. An insecticidal and acaricidal composition comprising (1) an insecticidally or acaricidally effective amount of a compound of the formula

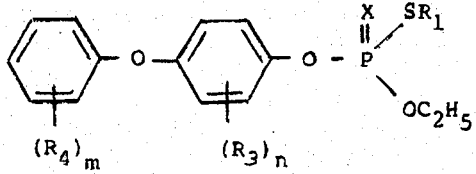

in which $R_1$ is methyl, ethyl, n-propyl, isopropyl, n-butyl, sec. butyl, n-pentyl or n-pentyl; each of $R_3$ and $R_4$ is hydrogen, chlorine, bromine or nitro; each of $m$ and $n$ is 1 or 2; and X is oxygen or sulphur; and (2) a carrier.

2. A method for controlling insects and acarids which comprises applying thereto an insecticidally or acaricidally effective amount of a compound according to claim 1.

3. A method according to claim 2 in which the compound is O-ethyl-S-n-propyl-O-(4-phenoxyphenyl)-thiophosphate.

4. A method according to claim 2 in which the compound is O-ethyl-S-n-propyl-O-[4-(4'-nitrophenoxy)-phenyl]-thiophosphate.

5. A method according to claim 2 in which the compound is O-ethyl-S-n-propyl-O-[4-(2'-nitrophenoxy)-phenyl]-thiophosphate.

6. A method according to claim 2 in which the compound is O-ethyl-S-n-propyl-O-[4-(4'-nitrophenoxy)-phenyl]-dithiophosphate.

7. A method according to claim 2 in which the compound is O-ethyl-S-n-propyl-O-[4-(2'-nitrophenoxy)-phenyl]-dithiophosphate.

8. A method according to claim 2 in which the compound is O-ethyl-S-n-propyl-O-[4-(4'-chlorophenoxy)-phenyl]-thiophosphate.

9. A method according to claim 2 in which the compound is O-ethyl-S-n-propyl-O-(2-chloro-4-phenoxyphenyl)-thiophosphate.

10. A method according to claim 2 in which the compound is O-ethyl-S-n-propyl-O-(2-bromo-4-phenoxyphenyl)-thiophosphate.

11. A method according to claim 2 in which the compound is O-ethyl-S-n-propyl-O-[2-bromo-4-(4'-chlorophenoxy)-phenyl]-thiophosphate.

12. A method according to claim 2 in which the compound is O-ethyl-S-n-propyl-O-[2,6-dibromo-4-(4'-bromophenoxy)-phenyl]-thiophosphate.

13. A method according to claim 2 in which the compound is O-ethyl-S-n-pentyl-O-(4-phenoxyphenyl)-thiophosphate.

14. A method according to claim 2 in which the compound is O-ethyl-S-sec.butyl-O-(4-phenoxyphenyl)-thiophosphate.

15. A method according to claim 2 in which the compound is O-ethyl-S-n-heptyl-O-(4-phenoxyphenyl)-thiophosphate.

* * * * *